US008168387B2

(12) United States Patent
Lefeuvre et al.

(10) Patent No.: US 8,168,387 B2
(45) Date of Patent: May 1, 2012

(54) OLIGONUCLEOTIDES, USE THEREOF, DETECTING METHOD AND KIT FOR DIAGNOSING THE PRESENCE OF H5 AND N1 GENES OF THE INFLUENZA A VIRUS

(75) Inventors: Aurélie Lefeuvre, Grenoble (FR); Jean-Noel Telles, Brignais (FR); Guy Vernet, Irigny (FR)

(73) Assignee: Biomerieux, Marcy l'Etoile (FR)

( * ) Notice: Subject to any disclaimer, the term of this patent is extended or adjusted under 35 U.S.C. 154(b) by 77 days.

(21) Appl. No.: 12/084,704

(22) PCT Filed: Nov. 23, 2006

(86) PCT No.: PCT/FR2006/051218

§ 371 (c)(1), (2), (4) Date: May 23, 2008

(87) PCT Pub. No.: WO2007/060366
PCT Pub. Date: May 31, 2007

(65) Prior Publication Data
US 2009/0305243 A1 Dec. 10, 2009

(30) Foreign Application Priority Data

Nov. 25, 2005 (FR) ..................................... 05 11974
Jan. 30, 2006 (FR) ..................................... 06 00843

(51) Int. Cl.
*C12Q 1/68* (2006.01)
*C12P 19/34* (2006.01)
*C07H 21/04* (2006.01)

(52) U.S. Cl. ...................... 435/6.12; 435/91.2; 536/24.3

(58) Field of Classification Search ............. 435/6, 91.2, 435/6.12; 536/24.3
See application file for complete search history.

(56) References Cited

U.S. PATENT DOCUMENTS 4,672,040 A 6/1987 Josephson
4,683,195 A 7/1987 Mullis et al.
4,683,202 A 7/1987 Mullis
4,800,159 A 1/1989 Mullis et al.
5,234,809 A 8/1993 Boom et al.
5,399,491 A 3/1995 Kacian et al.
5,750,338 A 5/1998 Collins et al.
6,576,448 B2 6/2003 Weissman et al.
2006/0257860 A1* 11/2006 Marlowe et al. .................. 435/5

FOREIGN PATENT DOCUMENTS

CN 1635163 A 7/2005
EP 0 201 184 A2 12/1986
EP 0 569 272 A1 11/1993
FR 2 607 507 6/1988
WO WO 90/01069 2/1990
WO WO 90/06995 6/1990
WO WO 91/02818 3/1991
WO WO 97/45202 12/1997
WO WO 99/15621 4/1999
WO WO 99/35500 7/1999
WO WO 99/53304 10/1999
WO WO 00/05338 2/2000
WO WO 00/60049 10/2000
WO WO 02/29118 A1 4/2002
WO WO 2005/121367 A1 12/2005

OTHER PUBLICATIONS

Zhou et al. Journal of Virology, 1999,vol. 73(4), p. 3366-3374.*
Lowe et al. Nucleic Acids Research, 1990, vol. 18(7), p. 1757-1761.*
The attached nucleic acid sequence search reports for SEQ ID NOL 1-4 and 7-8.*
Whiley, David M. et al. "A 5'-nuclease real-time reverse transcriptase-polymerase chain reaction assay for the detection of a broad range of influenza A subtypes, including H5N1." *Diagnostic Microbiology and Infectious Disease* 53 (2005) pp. 335-337.
Ng, Enders K.O. et al. "Influenza A H5N1 Detection." *Emerging Infectious Diseases* vol. 11, No. 8, Aug. 2005 pp. 1303-1305.
Payungporn, Sunchai et al. "Single-Step Multiplex Reverse Transcription-Polymerase Chain Reaction (RT-PCR) for Influenza A Virus Subtype H5N1 Detection." *Viral Immunology* vol. 17, No. 4, 2004 pp. 588-593.
Collins, Richard A. et al. "Detection of highly pathogenic and low pathogenic avian influenza subtype H5 (Eurasian lineage) using NASBA." *Journal of Virological Methods* 103 (2002) pp. 213-225.
Greijer, Astrid E. et al. "Multiplex real-time NASBA for monitoring expression dynamics of human cytomegalovirus encoded IE1 and pp67 RNA." *Journal of Clinical Virology* 24 (2002) pp. 57-66.
Egholm, Michael et al. "Peptide Nucleic Acids (PNA). Oligonucleotide Analogues with an Achiral Peptide Backbone." *Journal of American Chemical Society* vol. 114, No. 5, 1992 pp. 1895-1897.

(Continued)

*Primary Examiner* — Kenneth R. Horlick
*Assistant Examiner* — Joyce Tung
(74) *Attorney, Agent, or Firm* — Oliff & Berridge, PLC

(57) ABSTRACT

The present invention relates to a double pair of oligonucleotides for amplifying two target sequences located, respectively, in the H5 and N1 genes of the genome of the Influenza A virus, said oligonucleotides being of a length ranging between 10 and 50 nucleotides and comprising at least one fragment of 10 consecutive nucleotides derived from the following sequences:

```
SEQ ID No. 1:     TGTATGTTGTGGAATGGCA,

SEQ ID No. 2:     GCCGAATGATGCCATCAA,

SEQ ID No. 3:     CGTGGATTGTCTCCGAAA,
and

SEQ ID No. 4:     GGAATGCTCCTGTTATCCTGA
``` or the sequence complementary thereto.
The invention also relates to oligonucleotides for detecting amplicons, to the use of all these sequences, and to a method for detecting and a kit for diagnosing the presence of the H5 and N1 genes of the Influenza A virus.
The invention is particularly applicable in the field of diagnosis.

19 Claims, 1 Drawing Sheet

OTHER PUBLICATIONS

Sun, Bei-Wen et al. "Sequence and pH Effects of LNA-Containing Triple Helix-Forming Oligonucleotides: Physical Chemistry, Biochemistry, and Modeling Studies." *Biochemistry* vol. 43, No. 14, 2004 pp. 4160-4169.

Kievits, Tim et al. "NASBA™ isothermal enzymatic in vitro nucleic acid amplification optimized for the diagnosis of HIV-1 infection." *Journal of Virological Methods* vol. 35, 1991 pp. 273-286.

Payungporn, Sunchai et al. "Single step multiplex real-time RT-PCR for H5N1 influenza A virus detection." *Journal of Virological Methods* 131 (2006) pp. 143-147.

Collins, R. A. et al. "A NASBA Method to Detect High- and Low-Pathogenicity H5 Avian Influenza Viruses." *Avian Diseases* 47 (2003) pp. 1069-1074.

\* cited by examiner

Multiplex detection of H5 and N1 on 1000 copies of an H5N1 transcript

Fluorescence signal (rfu)

— Detection of N1 with CY5
— Detection of H5 with FAM

OLIGONUCLEOTIDES, USE THEREOF, DETECTING METHOD AND KIT FOR DIAGNOSING THE PRESENCE OF H5 AND N1 GENES OF THE INFLUENZA A VIRUS

The present invention relates to a method for labeling nucleic acids in the presence of at least one solid support.

The present invention relates to oligonucleotides for amplifying and detecting two target sequences located, respectively, in the H5 and N1 genes of the genome of the Influenza A virus.

The invention also relates to the use of these oligo-nucleotides, to a method of detection and to a kit for diagnosing the presence of the H5 and N1 genes of the Influenza A virus.

Among the conventional techniques routinely used for diagnosing flu, mention may be made of agglutination, inhibition of agglutination or diffusion in agar gel. These methods are commonly used and make it possible to characterize the flu virus A.

A possible alternative to these methods is viral culture in eggs at the embryonic stage or in MDCK cells, according to the protocol in the manual of the IOE [International Office for Epizootics]. However, several days are required in order to obtain the characterization results, this delay sometimes being incompatible with clinical needs or emergencies.

ELISA techniques for detecting antibodies or an antigen or immunofluorescence tests have also been enormously developed, but these “immunological” methods of detection are often less sensitive and less specific than conventional viral culture.

The recent emergence of a highly pathogenic form of the bird flu virus, subtype H5N1, has therefore strongly relaunched the need for a rapid, specific and highly sensitive diagnostic test. For this reason, the various methods listed above have been replaced gradually with “molecular” techniques, such as the RT-PCR technique (reverse transcription associated with a polymerase chain reaction). RT-PCR, which is more sensitive, does not require the presence of “viable” virus in the samples, and thus makes it possible to type and subtype the various forms of the flu virus. The development of this real time technique (“real time RT-PCR”) has also greatly promoted its use for diagnosing the type A virus.

For example, D. M. Whiley et al. describe, in a recent publication (Diagnostic Microbiology and Infectious Diseases (2005), in press), a test for detecting a broad spectrum of flu subtypes in clinical samples, based on an RT-PCR reaction involving a 5'-nuclease. Two oligonucleotides and a probe were chosen so as to be homologous to the gene encoding the M (matrix) protein of 23 subtypes of the A virus. This test thus makes it possible to detect the Influenza A virus in clinical samples, but does not, on the other hand, make it possible to precisely subtype the form involved.

E. K. O, Ng et al. have recently disclosed (Emerging Infectious Diseases (2005) vol. 11 (8), p. 1303-1305) a test based on a multiplex RT-PCR reaction comprising two steps, using two sets of oligonucleotides and of probes that have been labeled in order to specifically target two regions of the HA gene of H5N1. This has thus made it possible to develop a rapid and sensitive test for directly detecting the H5 subtype in human samples. This test has been validated on clinical samples originating from patients infected in Hong Kong and in Vietnam with the H5N1 subtype of the virus, but does not make it possible to diagnose directly which virus subtype is involved in the infection.

S. Payungporn et al. describe (Viral Immunology (2004) vol. 17 (4), p. 588-593 and Journal of Virological Methods (2005), in press) a method for simultaneously detecting the M, H5 and N1 sequences of the H5N1 subtype, based on a real time multiplex RT-PCR test and in a single step. Oligonucleotides corresponding to the M, H5 and N1 sequences and also various labeled TaqMan probes were selected and used in the test in order to simultaneously detect three fluorescent signals. The H5 and N1 oligonucleotides were chosen from invariant regions covering more than 50 known sequences specific for the H5N1 virus. However, it should be noted that this RT-PCR method, which is nonisothermal, is sometimes liable to contamination.

Another molecular method that can be used for detecting the presence of an infectious agent is the NASBA technique (Nucleic Acid Sequence-Based Amplification). For example, R. A. Collins et al. describe (Journal of Virological Methods (2002) vol. 103, p. 213-225 and Avian Diseases (2003) vol. 47 (3), p. 1069-1074) the detection of the H5 subtype of bird flu (detection of the highly pathogenic and weakly pathogenic subtype) using the NASBA technique coupled to an ECL (electro-chemiluminescence) detection system. The NASBA technique is a method of isothermal amplification of nucleic acids involving several enzymatic activities, which allows rapid detection of the H5 virus. The amplification of nucleic acids via this process is suitable for RNA genomes, such as the genome of the flu virus, by virtue of the introduction of the reverse transcription step directly into the amplification reaction. Nevertheless, even though the method described in this publication makes it possible to detect and distinguish the weakly pathogenic strains from the highly pathogenic strains, it does not make it possible to specifically identify the H5N1 form of the virus.

A test for identifying the Influenza A virus in its H5N1 form using a transcriptional amplification technique, which is particularly suitable for amplifying and detecting RNA viruses, is therefore still awaited. In addition, a multiplex test, i.e. a test which makes it possible to simultaneously amplify and detect the two H5 and N1 genes, the amplification technique being a transcriptional amplification technique such as NASBA, is particularly advantageous.

The present invention therefore relates to a double pair of oligonucleotides for amplifying two target sequences located, respectively, in the H5 gene and in the N1 gene of the genome of the Influenza A virus, the pair of oligonucleotides for amplifying the H5 gene consisting of:

- a first oligonucleotide of a length ranging between 10 and 50 nucleotides and comprising at least one fragment of 10 consecutive nucleotides derived from:
- SEQ ID No. 1: TGTATGTTGTGGAATGGCA, or the sequence complementary thereto, and
- a second oligonucleotide of a length ranging between 10 and 50 nucleotides and comprising at least one fragment of 10 consecutive nucleotides derived from:
- SEQ ID No. 2: GCCGAATGATGCCATCAA, or the sequence complementary thereto, while the pair of oligonucleotides for amplifying the N1 gene consists of:

- a first oligonucleotide of a length ranging between 10 and 50 nucleotides and comprising at least one fragment of 10 consecutive nucleotides derived from:
- SEQ ID No. 3: CGTGGATTGTCTCCGAAA, or the sequence complementary thereto, and
- a second oligonucleotide of a length ranging between 10 and 50 nucleotides and comprising at least one fragment of 10 consecutive nucleotides derived from:
- SEQ ID No. 4: GGAATGCTCCTGTTATCCTGA, or the sequence complementary thereto.

The invention may also relate to a pair of oligonucleotides for amplifying a target sequence located in the H5 gene of the genome of the Influenza A virus, the pair of oligonucleotides consisting of:
 a first oligonucleotide of a length ranging between 10 and 50 nucleotides and comprising at least one fragment of 10 consecutive nucleotides derived from:

SEQ ID No. 1: TGTATGTTGTGGAATGGCA, or the sequence complementary thereto, and a second oligonucleotide of a length ranging between 10 and 50 nucleotides and comprising at least one fragment of 10 consecutive nucleotides derived from:

SEQ ID No. 2: GCCGAATGATGCCATCAA, or the sequence complementary thereto.

Similarly, the invention can also cover a pair of oligonucleotides for amplifying a target sequence located in the N1 gene of the genome of the Influenza A virus, the pair of oligonucleotides consisting of:

a first oligonucleotide of a length ranging between 10 and 50 nucleotides and comprising at least one fragment of 10 consecutive nucleotides derived from:

SEQ ID No. 3: CGTGGATTGTCTCCGAAA, or the sequence complementary thereto, and a second oligonucleotide of a length ranging between 10 and 50 nucleotides and comprising at least one fragment of 10 consecutive nucleotides derived from:

SEQ ID No. 4: GGAATGCTCCTGTTATCCTGA, or the sequence complementary thereto.

In the three situations above, in the pair(s) of oligonucleotides, the first oligonucleotide additionally comprises a promoter sequence which can be recognized by a DNA-dependent RNA polymerase enzyme.

More specifically, the promoter sequence which can be recognized by a DNA-dependent RNA polymerase enzyme is a T7 polymerase.

In relation to the above two cases, when this oligonucleotide, to which the promoter sequence is added, makes it possible to amplify the target sequence located in the H5 gene, it essentially consists of the following sequence:

SEQ ID No. 5: aattctaatacgactcactatagggg TGTATGTTGTGGAATGGCA, or the sequence complementary thereto. The part of the sequence in lower case letters corresponds to the T7 promoter sequence.

In the same manner as above, when this oligonucleotide makes it possible to amplify the target sequence located in the N1 gene it essentially consists of the following sequence:

SEQ ID No. 6: aattctaatacgactcactataggggCGTGGATTGTCTCCGAAA, or the sequence complementary thereto.

In all situations, each oligonucleotide may be of a length ranging from between 12 and 30 nucleotides and comprising at least one fragment of 16 consecutive nucleotides, and preferably of a length ranging between 15 and 26 nucleotides and comprising at least one fragment of 18 consecutive nucleotides.

The invention also relates to a pair of oligo-nucleotides for use as a probe for detecting two target sequences located, respectively, in the H5 and N1 genes of the genome of the Influenza A virus, the probe for detecting the H5 gene consisting of:

SEQ ID No. 7: ACACCAAGTGTCAAACTCCAAT, or the sequence complementary thereto, while the probe for detecting the N1 gene consists of:

SEQ ID No. 8: GCGAAATCACATGTGTGTGCAGGGA, or the sequence complementary thereto, each sequence comprising at least one labeling means.

The invention may also relate to an oligonucleotide for use as a probe for detecting an amplified nucleic acid sequence resulting from the amplification of a target sequence located in the H5 gene of the genome of the Influenza A virus, said amplification being carried out by means of a pair of oligonucleotides as described above, the detection probe being of a length ranging between 10 and 50 nucleotides and comprising at least one fragment of 10 consecutive nucleotides derived from:

SEQ ID No. 7: ACACCAAGTGTCAAACTCCAAT, or the sequence complementary thereto, the sequence comprising at least one labeling means.

When it is desired to detect the N1 gene of the genome of the Influenza A virus, the invention recommends an oligonucleotide for use as a probe for detecting an amplified nucleic acid sequence resulting from the amplification of a target sequence located in this N1 gene, said amplification being carried out by means of a pair of oligonucleotides as described above, the detection probe being of a length ranging between 10 and 50 nucleotides and comprising at least one fragment of 10 consecutive nucleotides derived from:

SEQ ID No. 8: GCGAAATCACATGTGTGTGCAGGGA, or the sequence complementary thereto, the sequence comprising at least one labeling means.

In an advantageous embodiment of the invention, the detection probe consists of a "molecular beacon" subsequently known as molecular probe. The molecular probes are detection probes in the form of single-stranded oligonucleotides, which have a stem loop structure well-known to those skilled in the art. The loop contains a probe sequence complementary to the target sequence (amplicon in general), and the stem is formed by the hybridization of two sequences forming arms, which are each located at each end of the probe. A fluorophore is covalently bonded to the end of one of the two arms and a quencher (fluorescence absorber) is covalently bonded to the end of the other arm. The molecular probes do not fluoresce when they are free in solution. However, in the presence of complementary amplicons, when they hybridize to these targets, they undergo a conformational change which allows them to fluoresce. In the absence of targets, the stem keeps the fluorophore in close proximity with the quencher, thereby leading to the transfer of the fluorescence from the fluorophore to the quencher. Said quencher is a nonfluorescent chromophore which dissipates the energy received from the fluorophore as heat. When the probe encounters a molecular target, a probe-target hybrid is formed, which hybrid is longer and more stable than the hybrid created by the two arms of the stem. The rigidity and the length of the probe-hybrid hybrid prevent the simultaneous existence of the stem hybrid. Consequently, the molecular probe undergoes spontaneous conformational reorganization which forces the stem hybrid to dissociate and the fluorophore and the quencher to move away from one another, thereby restoring the fluorescence.

More specifically, the detection probe consists of a molecular probe preferably composed of:

SEQ ID No. 9: [6-FAM]-cgatcgACACCAAGTGTCAAACTCCAATcgatcg-[DabSyl], for detecting the H5 gene, SEQ ID No. 10: [6-FAM]-cgatcgGCGAAATCACATGTGTGTGCAGGGAcgatcg-[DabSyl], for detecting the N1 gene.

When the test that it is desired to carry out is a multiplex test where the detection of the H5 and N1 genes is simultaneous and carried out in a single container, it is advisable to use two different labels. Among the possible fluorescent labels, mention may be made, in a nonlimiting manner, of:

fluorescein (FAM)
tetrachloro-6-carboxyfluorescein (TET)
tetramethylrhodamine (TMR)
5-carboxyrhodamine 6G (RHD)
carboxyrhodamine (ROX), and
cyanin 5 (CY5).

Each of the two sequences SEQ ID Nos. 9 and 10 above will therefore be provided with one of these labels, the two labels used being different from one another in order to allow differentiation between the detected signals.

The invention also proposes the use of one or two pairs of oligonucleotides, as described above, in a reaction for the amplification of nucleic acids or as a probe for the detection of the genome of the Influenza A virus suspected of being present in a biological sample.

The invention also relates to a method for detecting nucleic acids of the Influenza A virus that may be present in a sample, in which the sample is subjected to a reaction for the amplification of nucleic acids using a pair of oligonucleotides, as described above, in the presence of the amplification reagents required for such an amplification, and the presence of amplicons of interest is detected.

This method of detection can be based on an RT-PCR amplification reaction.

Alternatively, this method of detection can be based on a transcriptional amplification technique. Preferably, this technique is the NASBA technique.

The invention also relates to a method for amplifying two H5 and N1 genes of the Influenza A virus that may be present in a sample, comprising the following steps:
  incubating the sample in an amplification buffer in the presence:
    of two amplification primers, each having a length ranging between 10 and 50 nucleotides, one additionally comprising a promoter sequence, the other of opposite polarity to the primer associated with the promoter sequence, in order to hybridize respectively upstream and downstream of a region of interest located in the H5 gene of the Influenza A virus,
    of two amplification primers, each having a length ranging between 10 and 50 nucleotides, one additionally comprising a promoter sequence, the other of opposite polarity to the primer associated with the promoter sequence, in order to hybridize respectively upstream and downstream of a region of interest located in the N1 gene of the Influenza A virus,
- adding the following reagents to the sample:
  - an enzyme having an RNA-dependant DNA polymerase activity,
  - an enzyme having a DNA-dependant DNA polymerase activity,
  - an enzyme having an RNase H activity,
  - an enzyme having a DNA-dependant RNA polymerase activity, and
- maintaining the reaction mix thus created under suitable conditions and for a period of time sufficient for an amplification to take place.

There are four enzymes listed above, but it is entirely possible to make use of one enzyme having two or even three of the abovementioned activities; in this case the use of three or even of two enzymes remains possible and covered by the invention. Furthermore, other elements required to establish an amplification are necessary, such as nucleotides. Such elements are well-known to those skilled in the art.

Finally, the invention proposes a kit for detecting the H5 and N1 genes of the Influenza A virus that may be present in a sample, containing:

- two pairs of amplification oligonucleotides or primers as defined above for carrying out the amplification of the two regions of interest H5 and N1,
- two oligonucleotides that are labeled or that can be labeled, as described above, and that have a nucleic acid sequence substantially complementary with at least one part of the amplified H5 or N1 nucleic acid sequence,
- reagents required for carrying out an amplification reaction.

The term "substantially complementary" is intended to mean that a hybridization is carried out between an oligonucleotide that is labeled or that can be labeled, otherwise referred to as detection probe, and at least one part of the amplified nucleic acid sequence or amplicon, this hybridization being sufficiently specific and selective to allow the detection of the amplicon of interest.

Furthermore, the reagents required for carrying out an amplification reaction are reagents for a NASBA amplification.

The term "detectable label" is intended to mean at least one label capable of directly generating a detectable signal. For example, the presence of biotin is considered to be direct labeling, since it is detectable even though it is possible to subsequently associate it with labeled streptavidin. A non-limiting list of these labels follows:

- enzymes which produce a signal that can be detected, for example, by colorimetry, fluorescence or luminescence, such as horseradish peroxydase, alkaline phosphatase, β-galactosidase or glucose-6-phosphate dehydrogenase,
- chromophores such as fluorescent, luminescent or dye compounds,
- electron dense groups that can be detected by electron microscopy or by virtue of their electrical properties such as conductivity, amperometry, voltametry or impedance,
- detectable groups, for example, the molecules of which are of sufficient sizes to induce detectable modifications of their physical and/or chemical characteristics; this detection can be carried out by optical methods such as diffraction, surface plasmon resonance, surface variation, contact angle variation, or physical methods such as atomic force spectroscopy, or tunnel effect,
- radioactive molecules such as $^{32}P$, $^{35}S$ or $^{125}I$.

Preferably, the label is not a radioactive label, so as to avoid the safety problems associated with these labels.

In a specific embodiment of the present invention, the label is detectable electrochemically, and in particular the label is a derivative of an iron complex, such as a ferrocene.

The term "nucleic acid" means a series of at least two deoxyribonucleotides or ribonucleotides, optionally comprising at least one modified nucleotide, for example, at least one nucleotide comprising a modified base, such as inosine, methyl-5-deoxycytidine, dimethylamino-5-deoxyuridine, deoxyuridine, diamino-2,6-purine or bromo-5-deoxyuridine, or any other modified base that allows hybridization. This polynucleotide can also be modified at the level of the internucleotide bond, for instance phosphorothioates, H-phosphonates or alkyl phosphonates, or at the level of the backbone, for instance, alpha-oligonucleotides (FR 2 607 507) or PNA (M. Egholm et al., J. Am. Chem. Soc., 114, 1895-1897, 1992) or 2'-O-alkyl riboses and LNAs (B W. Sun et al., Biochemistry, 4160-4169, 43, 2004). The nucleic acid may be natural or synthetic, an oligonucleotide, a polynucleotide, a nucleic acid fragment, a ribosomal RNA, a messenger RNA, a transfer RNA, or a nucleic acid obtained by means of an enzymatic amplification technique such as:

PCR (Polymerase Chain Reaction), described in U.S. Pat. No. 4,683,195, U.S. Pat. No. 4,683,202 and U.S. Pat. No. 4,800,159 and its derivative RT-PCR (Reverse Transcription PCR), in particular in a one-step format, as described in patent EP-B-0.569.272, LCR (Ligase Chain Reaction), disclosed, for example in patent application EP-A-0.201.184, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, TMA (Transcription Mediated Amplification) with U.S. Pat. No. 5,399,491, and RCA (Rolling Circle Amplification) (U.S. Pat. No. 6,576,448).

The term amplicons is then used to denote the nucleic acids generated by an enzymatic amplification technique.

Each of these modifications can be taken in combination.

The amplification and detection steps disclosed above can be preceded by a purification step. The term "purification step" is intended to mean in particular the separation between the nucleic acids of the microorganisms and the cellular constituents released in the lysis step which precedes the nucleic-acid purification. These lysis steps are well-known; by way of indicative example, use may be made of the lysis methods as described in patent applications:

WO-A-00/60049 on lysis by sonication,
WO-A-00/05338 on mixed magnetic and mechanical lysis,
WO-A-99/53304 on electrical lysis, and
WO-A-99/15621 on mechanical lysis.

Those skilled in the art may use other well-known methods of lysis, such as heat shock or osmotic shock or treatments with chaotropic agents, such as guanidium salts (U.S. Pat. No. 5,234,809).

This step generally makes it possible to concentrate the nucleic acids. By way of example, it is possible to use solid supports, such as magnetic particles (in this respect, see U.S. Pat. No. 4,672,040 and U.S. Pat. No. 5,750,338), and thus to purify the nucleic acids, which are attached to these magnetic particles, by means of a washing step. This nucleic acid purification step is particularly advantageous if it is desired to subsequently amplify said nucleic acids. A particularly advantageous embodiment of these magnetic particles is described in patent applications WO-A-97/45202 and WO-A-99/35500.

The term "solid support" as used here includes all materials to which a nucleic acid can be attached. Synthetic materials or natural materials, which have been optionally chemically modified, can be used as solid support, in particular polysaccharides, such as cellulose-based materials, for example, paper, cellulose derivatives such as cellulose acetate and nitrocellulose or dextran; polymers, copolymers, in particular based on styrene-type monomers, natural fibers such as cotton, and synthetic fibers such as nylon; mineral materials such as silica, quartz, glasses, ceramics; latices; magnetic particles; metal derivatives, gels, etc. The solid support may be in the form of a microtitration plate, of a membrane, of a particle or of a substantially flat glass or silicon plate, or derivatives.

It is possible to carry out the entire protocol (from the sample taken to the amplicons ready to be hybridized) in one and the same tube, processed manually or in an automated machine.

The attached examples represent specific embodiments and cannot be considered to limit the scope of the present invention.

Several controls were carried out in these examples. First of all, a negative control with water; in this case, no signal for either H5 or for N1 is detected. Secondly, a specificity control with Influenza H3N2 RNA; here again, no signal was detected for either H5 or for N1.

EXAMPLE 1

Experiment to Evaluate the H5N1 Primers on an H5N1 RNA Originating from a Clinical Sample from Asia The sequences of the pairs of oligonucleotides (N1_P1 and N2_P2, used for amplifying and detecting the N1 sequence, and H5_P1 and H5_P2, used for amplifying and detecting the H5 sequence) and of the detection probes present in the form of molecular probes (molecular probe N1 and molecular probe H5) are indicated below:

N1 P2    5'-GGAATGCTCCTGTTATCCTGA-3'

N1 P1    5'-AATTCTAATACGACTCACTATAGGGGCGTGGATTGTCTC CGAAA3'

N1 probe 5'-CGATCGGCGAAATCACATGTGTGTGCAGGGACGATCG-3'

H5 P2    5'-GCCGAATGATGCCATCAA-3'

H5 P1    5'-AATTCTAATACGACTCACTATAGGGGTGTATGTTGTGG AATGGCA-3'

H5 probe 5'-CGATCGACACCAAGTGTCAAACTCCAATCGATCG-3'

The sequence indicated in bold corresponds to the T7 promoter sequence, recognized by the T7 RNA polymerase, and is found in the P1 oligonucleotides for carrying out the NASBA technique.

The sample is processed using the miniMAG system, as described in the operating protocol. The kits used are:

NucliSens Lysis Buffer, bioMérieux B. V. (Boxtel, Holland), Batch No. 200295, and NucliSens Magnetic Extraction Reagents, bioMérieux B. V., Batch No. #200297.

Operating Protocol for the Detection Test:

According to the instructions of the NucliSens EasyQ Basic Kit (bioMérieux B. V., Boxtel, Holland, Batch No. #285006) two reaction mixes, one serving to amplify and detect the H5 sequence ("mix H5") and the other serving to amplify and detect the N1 sequence ("mix N1") were prepared. Briefly, 11 µl of water, 13 µl of KCl at 1.2 M, 4 µl of each oligonucleotide (H5_P1 and H5_P2 or N1_P1 and N1_P2, stock solution at 10 µM) and 0.8 µl of the appropriate detection probe (the molecular probe H5 or the molecular probe N1, stock solution at 2 µM) were added to 64 µl of diluent. A volume of 10 µl of each mix was then added to 5 µl of the RNA target. In parallel, a solution of enzymes was prepared, and 5 µl of this solution were added to the reaction mix in the tube for a final volume of 20 µl. The samples were then placed under the reaction conditions recommended by the NucliSens EasyQ Basic Kit in order to allow the amplification and detection of the sequences of interest by the isothermal NASBA technique (Kievits, T et al. J. Virol. Methods (1991) vol. 35(3), p. 273-286).

In order to validate this detection test, the RNA targets used were the following:

H5N1: Influenza A subtype H5N1 Vietnam 1194/2004
Influenza A: subtype H3N2,
H5 control RNA: subtype H5N3, Influenza B.

The appropriate (positive and negative) controls were included in the test.

After amplification and detection on the NucliSens EasyQ system, the following results were obtained:

| Virus | NASBA H5 Results | NASBA N1 Results |
|---|---|---|
| Negative control | Negative | Negative |
| Influenza A H3N2 | Negative | Negative |
| Negative | Negative | Negative |
| Flu A H5N1 Vietnam 1194/2004 | Positive | Positive |
| Negative control | Negative | Negative |
| Flu A H5N1 Vietnam 1194/2004 | Positive | Positive |
| Flu A H5N3 Duck control virus | Positive | Negative |

These results show that the H5N1 detection probes and oligonucleotides are specific and indeed detect their respective targets H5 and N1.

EXAMPLE 2

Experiment to Evaluate the Detection Probes and Primers for H5N1 in a Multiplex Test In the case of the multiplex, the molecular probe N1 used is labeled with CY5, whereas the molecular probe H5 remains labeled with FAM.

For information, in order to demonstrate the functionality of our sequences in a multiplex test, the target used is a synthetic transcript, which was constructed from the recombinant H5N1 RNA. It is an RNA, which comprises only the H5 and N1 regions. It is used as reference RNA for evaluating the performance levels of our amplification primers and detection probes for H5 and N1 (since it is a synthetic transcript, it is available in large amount, which means that the recombinant H5N1 RNA, which is very precious, does not have to be used).

According to the instructions of the NucliSens EasyQ Basic Kit (bioMérieux B. V., Boxtel, Holland, Batch No. #285006), a single reaction mix for simultaneously detecting the H5 gene and the N1 gene is prepared. Briefly, 11 µl of water, 13 µl of KCl at 1.2 M, 8 µl of a solution of oligonucleotides and of molecular probes (containing the oligonucleotides H5_P1 and H5_P2 for H5 at 5 µM, the oligonucleotides N1_P1 and N1_P2, for N1 at 20 µM, the molecular probe H5-FAM at 2 µM and the molecular probe N1-CY5 at 2 µM) were added to 64 µl of diluent. A volume of 10 µl of the mix was then added to 5 µl of the RNA target (H5N1 transcript at 1000 copies/NASBA).

The difference in concentration between the H5 primers and the N1 primers is approximately inversely proportional to the difference in sensitivity. The concentration of H5 primers is therefore four times lower than that of N1 primers.

In parallel, a solution of enzymes was prepared, and 5 µl of this solution were added to the reaction mix in the tube, for a final volume of 20 µl. The samples were then placed under the reaction conditions recommended by the NucliSens EasyQ Basic Kit in order to allow the amplification and detection of the sequences of interest by the isothermal NASBA technique (Kievits, T et al. J. Virol. Methods (1991) vol. 35(3), p. 273-286). The results can be seen in FIG. 1. These results show that the simultaneous detection of H5 and N1 in a single tube functions very well on a synthetic transcript.

The invention claimed is:

1. Two pairs of oligonucleotides for amplifying two target sequences located, respectively, in the H5 gene and in the N1 gene of the genome of the Influenza A virus, the pair of oligonucleotides for amplifying the H5 gene consisting of:
a first oligonucleotide comprising a target binding sequence consisting of SEQ ID No. 1 or the sequence fully complementary thereto, and
a second oligonucleotide comprising a target binding sequence consisting of SEQ ID No. 2 or the sequence fully complementary thereto, while the pair of oligonucleotides for amplifying the N1 gene consists of:
a first oligonucleotide comprising a target binding sequence consisting of SEQ ID No. 3 or the sequence fully complementary thereto, and
a second oligonucleotide comprising a target binding sequence consisting of SEQ ID No. 4 or the sequence fully complementary thereto.

2. A pair of oligonucleotides for amplifying a target sequence located in the H5 gene of the genome of the Influenza A virus, the pair of oligonucleotides consisting of:
- a first oligonucleotide comprising a target binding sequence consisting of SEQ ID No. 1 or the sequence fully complementary thereto, and a second oligonucleotide comprising a target binding sequence consisting of SEQ ID No. 2 or the sequence fully complementary thereto.

3. A pair of oligonucleotides for amplifying a target sequence located in the N1 gene of the genome of the Influenza A virus, the pair of oligonucleotides consisting of:

a first oligonucleotide comprising a target binding sequence consisting of SEQ ID No. 3 or the sequence fully complementary thereto, and a second oligonucleotide comprising a target binding sequence consisting of SEQ ID No. 4 or the sequence fully complementary thereto.

4. The two pairs of oligonucleotides as claimed in claim 1, wherein each first oligonucleotide additionally comprises a promoter sequence which can be recognized by a DNA-dependent RNA polymerase enzyme.

5. The two pairs of oligonucleotides as claimed in claim 4, wherein the promoter sequence which can be recognized by a DNA-dependent RNA polymerase enzyme is a T7 polymerase.

6. The two pairs of oligonucleotides as claimed in claim 4, in which the first oligonucleotide for amplifying the H5 gene consists of the following sequence:

SEQ ID No. 5 or the sequence fully complementary thereto.

7. The two pairs of oligonucleotides as claimed in claim 4, in which the first oligonucleotide for amplifying the N1 gene consists of the following sequence:

SEQ ID No. 6 or the sequence fully complementary thereto.

8. A method for detecting nucleic acids of the Influenza A virus that may be present in a sample, the method comprising:

subjecting the sample to a reaction for the amplification of nucleic acids using the two pairs of oligonucleotides as claimed in claim 1, in the presence of amplification reagents required for amplification, and detecting two target sequences located, respectively in the H5 and N1 genes of the Influenza A virus, wherein:

a detection probe for detecting the H5 gene comprises a target binding sequence consisting of SEQ ID No. 7 or the sequence fully complementary thereto, a detection probe for detecting the N1 gene comprises a target binding sequence consisting of SEQ ID No. 8 or the sequence fully complementary thereto, and each detection probe comprises at least one labeling means.

9. A method for detecting nucleic acids of the Influenza A virus that may be present in a sample, the method comprising:

subjecting the sample to a reaction for the amplification of nucleic acids using the pair of oligonucleotides as claimed in claim 2, in the presence of amplification reagents required for amplification, and detecting a target sequence located in the H5 gene of the Influenza A virus using a detection probe comprising a target binding sequence consisting of SEQ ID No. 7 or the sequence fully complementary thereto, the detection probe comprising at least one labeling means.

10. A method for detecting nucleic acids of the Influenza A virus that may be present in a sample, the method comprising:

subjecting the sample to a reaction for the amplification of nucleic acids using the pair of oligonucleotides as claimed in claim 3, in the presence of amplification reagents required for amplification, and detecting a target sequence located in the N1 gene of the Influenza A virus using a detection probe comprising a target binding sequence consisting of SEQ ID No. 8 or the sequence fully complementary thereto, the detection probe comprising at least one labeling means.

11. The method of claim 8, wherein the detection probe is a molecular probe comprising a molecular beacon.

12. A method for the amplification of nucleic acids, the method comprising combining the two pairs of oligonucleotides claimed in claim 1 with nucleic acids from a biological sample suspected of comprising the Influenza A virus, and amplifying at least one nucleic acid under conditions sufficient for amplification when at least one of the H5 and N1 genes are present.

13. A method for detecting nucleic acids of the Influenza A virus that may be present in a sample, the method comprising subjecting the sample to a reaction for the amplification of nucleic acids using the two pairs of oligonucleotides as claimed in claim 1, in the presence of amplification reagents required for amplification, and detecting the presence of amplicons of interest when at least one of the H5 and N1 genes are present.

14. The method as claimed in claim 13, wherein the amplification reaction used is an RT-PCR.

15. The method as claimed in claim 13, wherein the amplification reaction used is a transcriptional amplification technique.

16. The method as claimed in claim 15, wherein the amplification reaction used is the NASBA technique.

17. A method for amplifying H5 and N1 genes of the Influenza A virus that may be present in a sample, comprising the following steps:

incubating the sample in an amplification buffer in the presence:

of two amplification primers consisting of a first oligonucleotide comprising a target binding sequence consisting of SEQ ID No. 1, or the sequence fully complementary thereto, and a second oligonucleotide comprising a target binding sequence consisting of SEQ ID No. 2, or the sequence fully complementary thereto, one additionally comprising a promoter sequence, the other of opposite polarity to the primer associated with the promoter sequence, in order to hybridize respectively upstream and downstream of a region of interest located in the H5 gene of the Influenza A virus, of two amplification primers consisting of:

a first oligonucleotide comprising a target binding sequence consisting of SEQ ID No. 3, or the sequence fully complementary thereto, and a second oligonucleotide comprising a target binding sequence consisting of SEQ ID No. 4, or the sequence fully complementary thereto, wherein one additionally comprises a promoter sequence, and the other of opposite polarity to the primer associated with the promoter sequence, in order to hybridize respectively upstream and downstream of a region of interest located in the N1 gene of the Influenza A virus, adding the following reagents to the sample:

an enzyme having an RNA-dependant DNA polymerase activity, an enzyme having a DNA-dependant DNA polymerase activity, an enzyme having an Rnase H activity, and
an enzyme having a DNA-dependent RNA polymerase activity, and
maintaining a reaction mix thus created under suitable conditions and for a period of time sufficient for an amplification to take place.

18. A kit for detecting the H5 and N1 genes of the Influenza A virus that may be present in a sample, containing:
   the two pairs of oligonucleotides as claimed in claim 1,
   an oligonucleotide for detecting the H5 gene comprising a target binding sequence consisting of SEQ ID No. 7 or the sequence fully complementary thereto, and
   an oligonucleotide for detecting the N1 gene comprising a target binding sequence consisting of SEQ ID No. 8 or the sequence fully complementary thereto, and
   reagents required for carrying out an amplification,
   wherein each detection oligonucleotide comprises at least one labeling means.

19. The kit as claimed in claim 18, in which the reagents required for carrying out an amplification reaction are reagents for a NASBA amplification.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Influenza A virus

<400> SEQUENCE: 1
tgtatgttgt ggaatggca                                                 19

<210> SEQ ID NO 2
<211> LENGTH: 18
<212> TYPE: DNA
<213> ORGANISM: Influenza A virus

<400> SEQUENCE: 2
gccgaatgat gccatcaa                                                  18

<210> SEQ ID NO 3
<211> LENGTH: 18
<212> TYPE: DNA
<213> ORGANISM: Influenza A virus

<400> SEQUENCE: 3
cgtggattgt ctccgaaa                                                  18

<210> SEQ ID NO 4
<211> LENGTH: 21
<212> TYPE: DNA
```

```
<213> ORGANISM: Influenza A virus

<400> SEQUENCE: 4
ggaatgctcc tgttatcctg a                                      21

<210> SEQ ID NO 5
<211> LENGTH: 45
<212> TYPE: DNA
<213> ORGANISM: Influenza A virus

<400> SEQUENCE: 5
aattctaata cgactcacta tagggtgta tgttgtggaa tggca             45

<210> SEQ ID NO 6
<211> LENGTH: 44
<212> TYPE: DNA
<213> ORGANISM: Influenza A virus

<400> SEQUENCE: 6
aattctaata cgactcacta tagggcgtg gattgtctcc gaaa              44

<210> SEQ ID NO 7
<211> LENGTH: 22
<212> TYPE: DNA
<213> ORGANISM: Influenza A virus

<400> SEQUENCE: 7
acaccaagtg tcaaactcca at                                     22

<210> SEQ ID NO 8
<211> LENGTH: 25
<212> TYPE: DNA
<213> ORGANISM: Influenza A virus

<400> SEQUENCE: 8
gcgaaatcac atgtgtgtgc aggga                                  25

<210> SEQ ID NO 9
<211> LENGTH: 34
<212> TYPE: DNA
<213> ORGANISM: Influenza A virus

<400> SEQUENCE: 9
cgatcgacac caagtgtcaa actccaatcg atcg                        34

<210> SEQ ID NO 10
<211> LENGTH: 37
<212> TYPE: DNA
<213> ORGANISM: Influenza A virus

<400> SEQUENCE: 10
cgatcggcga aatcacatgt gtgtgcaggg acgatcg                     37
```